United States Patent [19]

Münch

[11] Patent Number: 4,468,200
[45] Date of Patent: Aug. 28, 1984

[54] HELICAL MANDIBULAR IMPLANT

[75] Inventor: Manfred Münch, Nürtingen, Fed. Rep. of Germany

[73] Assignee: Feldmühle Aktiengesellschaft, Düsseldorf, Fed. Rep. of Germany

[21] Appl. No.: 549,585

[22] Filed: Nov. 7, 1983

[30] Foreign Application Priority Data

Nov. 12, 1982 [DE] Fed. Rep. of Germany ....... 3241963

[51] Int. Cl.³ .......................... A61F 5/04; A61F 1/00
[52] U.S. Cl. ........................................ 433/174; 3/1.9; 3/1; 128/92 C
[58] Field of Search ............................... 433/171-176; 3/1, 1.9

[56] References Cited

U.S. PATENT DOCUMENTS

| | | | |
|---|---|---|---|
| 3,579,831 | 5/1971 | Stevens | 433/174 |
| 3,849,887 | 11/1974 | Brainin | 433/173 |
| 4,103,422 | 8/1978 | Weiss et al. | 433/174 |
| 4,215,986 | 8/1980 | Riess | 433/173 |

Primary Examiner—Richard J. Apley
Assistant Examiner—David J. Isabella
Attorney, Agent, or Firm—Max Fogiel

[57] ABSTRACT

Mandibular implant of ceramic material in which a bottom portion for anchoring in the mandible has a substantially conical helix shape rounded off at the end. An upper portion has a concave section for receiving an epithelial sleeve by the concave section and an opening to accept a denture support. There are provided at least one annular expansion and at least two annular notches adjacent the upper portion and the bottom portion. The annular expansion has a diameter which is shorter than the diameter of the crest of the thread at the uppermost turn on the bottom portion of the implant.

4 Claims, 7 Drawing Figures

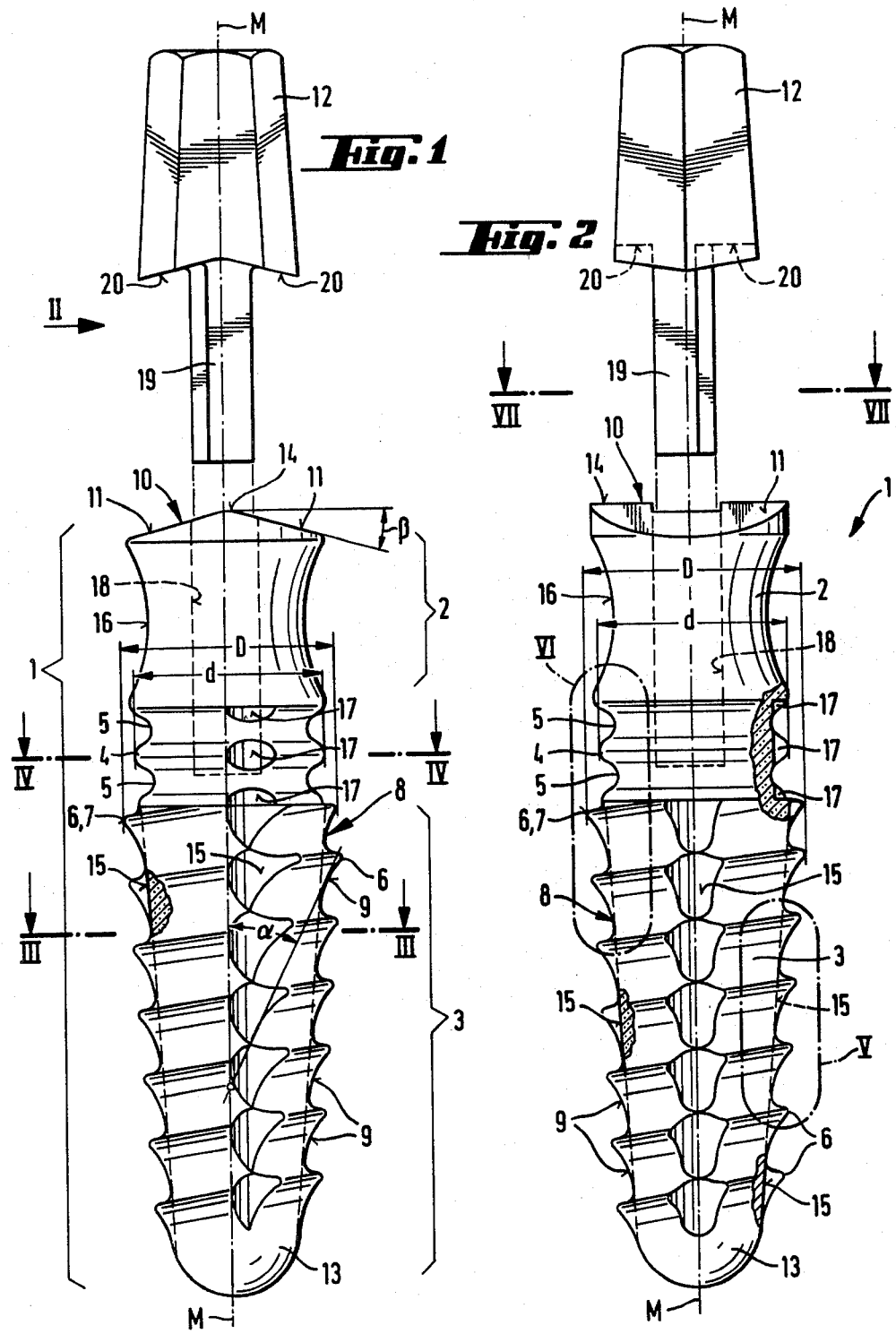

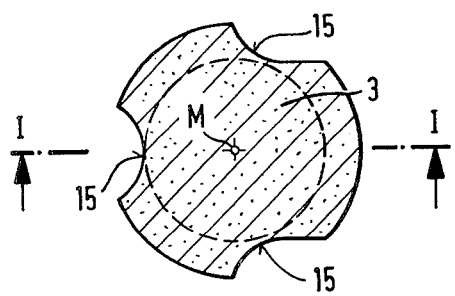
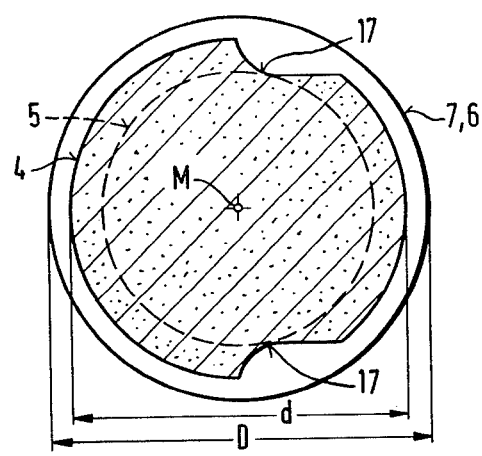
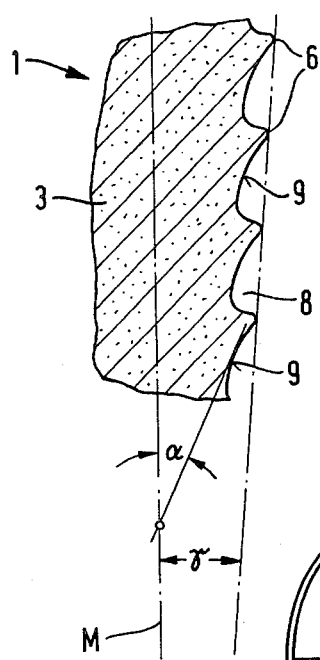
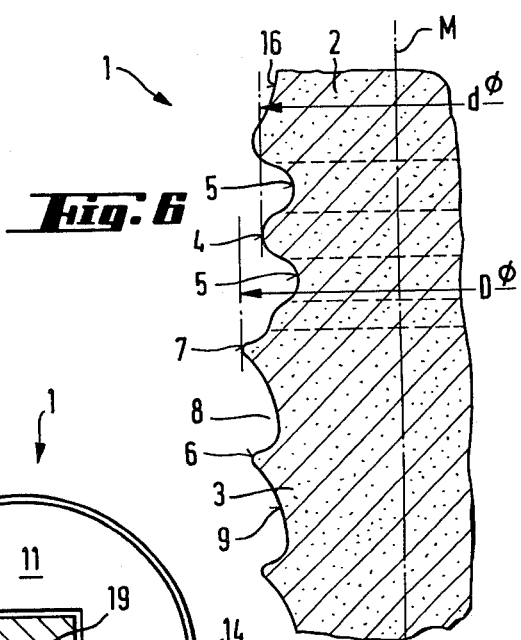
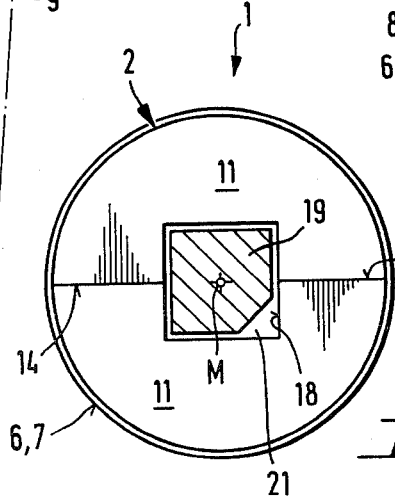

HELICAL MANDIBULAR IMPLANT

BACKGROUND OF THE INVENTION

The object of the present invention is a mandibular implant of ceramic material that is shaped at the bottom, where it is anchored in the mandible, like a conical helix rounded off at the end and that has a concave section to receive the epithelial sleeve and an opening to accept a denture support at the top.

Helical mandibular implants with a denture support at the top have long been known. German OS No. 2 600 639 describes an insert that is to be implaced in the jaw immediately after extraction of a tooth. The part of the insert described coverges in the shape of a cone that is rounded off at the bottom. One disadvantage of this insert is that the threading is rounded off almost to a circle and does not impede the insert working itself out. Another drawback is its single-phase design. The section to be anchored in the jaw and the actual denture support are in one piece. Thus, healing cannot proceed uninterrupted. The denture support projects out of the crest of the jaw. It constitutes an obstacle to the instinctive motion of the tongue. This displaces the implant, even though minimally, and perceptibly inhibits the healing process.

Another version is proposed in German OS No. 3 043 336. It is an implant made if necessary of a ceramic material in the shape of a conical helix with serrated threading. It has a concave section at the top to receive the epithelial sleeve and is rounded off at the bottom. A denture support can be inserted at the top, resting in a plastic mount that cushions the masticatory forces.

These known implants have one overall drawback consequent to implacement. Although, as the maxillary tissue regenerates and accumulates, it surrounds the conical section of the helix, it does not always prevent the implant from working loose and hence out of the jaw. In the implant known from OS No. 2 600 639 this is because the conical helix continues all the way up to the denture support. In that known from OS No. 3 043 336 it is because it continues up to the top, with the concave section. These implants rest accordingly in what is practically a funnel. The bone and connective tissue cannot reliably prevent an upward displacement.

Another drawback to the implant known from OS No. 3 043 336 derives from the serrated threading. The angle of the sides of the thread to the center line of the implant opens toward the bottom. This threading is intended to provide support. In spite of the cushioning of masticatory forces provided by the plastic mount, however, peaks of tension occur at the crests of the thread. These peaks severely stress the bone tissue and can loosen the implant. The serrated threading can also not prevent the implant from working out of the jaw.

SUMMARY OF THE INVENTION

The object of the present invention is a mandibular implant without these disadvantages. An implant in accordance with the invention will be anchored considerably more effectively in the mandible by the bone tissue regenerating around it. The invention solves the urgent problem of augmenting the initial stability of a newly implaced implant. The invention will prevent peaks of tension from occurring at the crests of the thread during mastication. This accelerates the healing process and prevents the implant from working loose. An implant in accordance with the invention can be implaced immediately after a tooth has been extracted. It will not be displaced by the unavoidable instinctive movements of the tongue that prolong the healing process.

This object is attained in accordance with the invention in a mandibular implant of ceramic material that is shaped at the bottom, where it is anchored in the mandible, like a conical helix rounded off at the end and that has a concave section to receive the epithelial sleeve and an opening to accept a denture support at the top because there are at least one annular expansion and at least two annular notches between the top and the bottom, which is a conical helix, the diameter of the annular expansion being shorter than that of the crest of the thread at the uppermost turn on the bottom of the implant.

At least one annular expansion and at least two annular notches between the top and the bottom, which is a conical helix, allow fibers of connective tissue to grow above the crest of the uppermost thread to below the top with its concave section. This prevents the formation of a funnel that would loosen the implant and accelerates healing. The annular notches and expansion below the top are especially effective in preventing the funnels that form in connection with the known implants.

Another advantage of a conicular-helix implant with the annular notches and expansion in accordance with the invention over known cylindrical-helix implants is that it can be implaced immediately after extraction of a tooth. The known implants cannot be implaced at least until the socket fills up with new bone or connective tissue, and a hole must then be drilled to accept the implant.

One especially practical embodiment of the invention ensures reliable anchoring even during the healing process. The bottom of this implant has serrated threading with sides at an angle $\alpha$, of less than 90° preferably 20°–40°, to the center line of and open toward the top of the implant.

This threading extremely effectively counteracts any tensile forces that occur. Furthermore, the major stress exercised on the implant as the result of masticatory forces is tangentially diverted through the overall conical surface and threading in the form of a force parallelogram onto the adjacent bone. This reliably prevents overstress. Thus the present invention follows the same principle followed by natural teeth. Histological studies have demonstrated that fibers of connective tissue applying themselves tangentially to the implant promote the mechanism of retention. These correspond to the desmodondum of the natural tooth, which also exerts itself tangentially.

The roof of the top of an especially preferred embodiment of the present invention consists of two semicircular surfaces that slope down laterally at an angle $\beta$ of 13°–18° from the peak. This prevents a mandibular implant in accordance with the invention from being disturbed by instinctive motions of the tongue. The disadvantage of known mandibular implants, especially those in which the part to be anchored in the jaw and the denture support are in one piece, is that instinctive motions of the tongue displace the denture support and disrupt the healing process.

An implant in accordance with the invention is implaced with the roof peak that separates the two semicircular surfaces and has the same diameter as the roof positioned in the mandibular crest mesially and distally. The semicircle of each surface faces buccally and lingually or palatinally.

Additional retention recesses are added to the annular notches and expansion in another practical embodiment of the invention. They further promote ingrowth of the implant and improve its anchoring in the mandibular crest.

Some preferred embodiments of the invention will now be described with reference to the attached drawings, wherein:

BRIEF DESCRIPTION OF THE DRAWINGS

FIG. 1 is a lateral view of and a broken section through a mandibular implant in accordance with the invention accompanied by a denture support, which is represented as separated from the implant, FIG. 2 a view from the direction indicated by the arrow II in FIG. 1 of and a broken section through the same implant, FIG. 3 a section along the line III—III in FIG. 1, FIG. 4 a section along the line IV—IV in FIG. 1, FIG. 5 a larger-scale broken section through the area indicated by V in FIG. 2, FIG. 6 a larger-scale broken section through the area indicated by VI in FIG. 2, and FIG. 7 a view from the plane VII—VII in FIG. 2.

DETAILED DESCRIPTION OF THE PREFERRED EMBODIMENTS

FIG. 1 illustrates a mandibular implant 1 in accordance with the present invention with a rounded end 13 at the bottom 3. Bottom 3 has serrated thread sections 8, illustrated in larger scale in FIG. 5. Between top 2, which has a concave section 16, and bottom 3 are two annular notches 5 and an annular expansion 4. Newly formed bone will grow over the notches and expansion. The roof 10 of top 2 consists of two semicircular surfaces 11. Surfaces 11 merge in a peak 14 that is elevated at an angle β of 15°. Peak 14 equals the diameter of top 2. When the implant is inserted in the jaw, peak 14 will be oriented mesially and distally. Retention recesses 17 in annular expansion 4 and annular notches 5 improve anchoring. The diameter d of annular expansion 4 is, in accordance with the invention, shorter than the diameter D of the uppermost turn 7 of the thread section of the conical-helix bottom 3 as measured at the crest 6 of turn 7. Thread sections 6, 8, and 9 have a conicity γ.

FIG. 2 illustrates the mandibular implant 1 in FIG. 1 from another angle. A discharge channel 15 parallel to the longitudinal axis 24 of bottom 3 diverts secretions from the wound. Since channel 15 is in the form of a groove, it also increases retentional stability. A denture support 12 is fastened by a pin 19 into an opening in top 2. The bottom surface 20 of denture support 12 fits snugly over roof 10. The shape of opening 18 and pin 19 will be described in greater detail later herein with reference to FIG. 7.

FIG. 3 illustrates a section along the line III—III in FIG. 1 with further discharge channel 15.

FIG. 4 illustrates the retention recesses 17 in the vicinity of annular expansion 4.

FIG. 5 is an enlarged detail of area V in FIG. 2. The sides of serrated threading 8 are at an angle α, preferably 20°–40°, to the center line of and opening toward the top of the implant. The crests 6 of the thread suspend mandibular implant 1 in the newly forming connective tissue.

FIG. 6 is a highly magnified detail of a section of area VI in FIG. 2. It illustrates the annular notches 5 below the top 2 with its concave section 16 and above bottom 3 and the annular expansion 4 between annular notches 5.

FIG. 7 illustrates the square cross-section of the opening 18 that accepts the pin 19 of denture support 12. Pin 19 has a pentagonal cross-section produced by leaving off one corner of the square cross-section of the hole to provide a channel 21 for administrating adhesives.

The present specification and claims are of course intended solely as illustrative and must not be understood as limiting the invention in any way. Modifications and changes may accordingly be made in the invention without departing from its theory and scope.

I claim:

1. A mandibular implant comprising upper, intermediate and bottom portions, said bottom portion being substantially conical and including helical threads formed on the surface thereof beginning at a rounded end tip and spiralling up to and adjacent said intermediate portion for anchoring said implant in the mandibles; said upper portion having a concave lateral surface for receiving an epthelial sleeve and further including a bore formed at its top end to receive a denture support member; said intermediate portion having at least one annular notches formed therein to allow fibers of connective tissue to grow into said notches thus preventing loosening of said implant, said annular expansion member having a diameter less than the diameter of said thread at an upper-most turn located on said bottom portion.

2. Mandibular implant as defined in claim 1, wherein said bottom portion has threads with a serrated contour when viewed in longitudinal section and with sides at an angle of less than 90° to a longitudinal axis of the implant and open toward the top of the implant.

3. Mandibular implant as defined in claim 2, wherein said angle is between 20° and 40°.

4. Mandibular implant as defined in claim 1, wherein said upper portion has a roof comprising two semicircular surfaces sloping down laterally at an angle of 13° to 18° from the peak.

* * * * *